US00PP25963P3

(12) United States Plant Patent
Opgenorth

(10) Patent No.: US PP25,963 P3
(45) Date of Patent: Sep. 29, 2015

(54) ***HEMIGRAPHIS ALTERNATA* PLANT NAMED 'HEGHE02'**

(50) Latin Name: *Hemigraphis alternata*
Varietal Denomination: HEGHE02

(71) Applicant: Costa Farms, LLC, Miami, FL (US)

(72) Inventor: Jayson Opgenorth, Apopka, FL (US)

(73) Assignee: Costa Farms LLC, Miami, FL (US)

( * ) Notice: Subject to any disclaimer, the term of this patent is extended or adjusted under 35 U.S.C. 154(b) by 180 days.

(21) Appl. No.: 13/987,387

(22) Filed: Jul. 19, 2013

(65) Prior Publication Data
US 2015/0026852 P1 Jan. 22, 2015

(51) Int. Cl.
*A01H 5/00* (2006.01)

(52) U.S. Cl.
USPC ..... Plt./373

(58) Field of Classification Search
USPC ..... Plt./373, 263.1
See application file for complete search history.

*Primary Examiner* — June Hwu
(74) *Attorney, Agent, or Firm* — Samuel R. McCoy, Jr.

(57) ABSTRACT

'HEGHE02' is a distinctive variety of *Hemigraphis alternata* which is characterized by yellow and green leaf variegation, large leaf size, and a dense growth habit.

3 Drawing Sheets

Latin name of the genus and species: The Latin name of the genus and species of the novel variety disclosed herein is *Hemigraphis alternata.*

Variety denomination: The inventive variety of *Hemigraphis alternata* disclosed herein has been given the variety denomination 'HEGHE02'.

BACKGROUND OF THE INVENTION

The present invention relates to a new and distinct perennial variety of *Hemigraphis alternata,* which has been given the variety denomination of 'HEGHE02'. Its market class is that of an herbaceous perennial groundcover. The primary intended use of *Hemigraphis alternata* is as a decorative foliage plant in ornamental containers, but it may also be used as a spreading groundcover in warm, tropical climates. The species is known for its attractive foliage color which can be described as an iridescent, metallic purple upper leaf surface and a solid purple lower leaf surface.

Parentage: In February 2012, a spontaneous mutation of *Hemigraphis alternata* 'Exotica' (unpatented), possessing yellow and green foliage variegation, was discovered at a commercial greenhouse facility in Apopka, Fla. in a production crop of 2,545 nursery pots of *Hemigraphis alternata* 'Exotica'. All other progeny in the crop maintained the foliage color that is typical of the parent. Each pot within the crop contained multiple vegetative cutting progeny and, upon closer examination, it was determined that the variegated mutation, or "sport", resulted from a mutation on a lateral branch of one such vegetative cutting. Said sport was removed from the mother plant as a vegetative cutting in March 2012 and rooted in a separate area so its growth could be monitored. Subsequent vegetative cuttings were taken and rooted. It was found that the sport remained true to type. The new plant was finally selected in December 2012 and given the name 'HEGHE02'.

Asexual Reproduction: 'HEGHE02' was first propagated asexually by stem cuttings at a commercial greenhouse in Apopka, Fla. and has since been asexually propagated through numerous successive generations with a total of 9,770 resulting progeny. The distinctive characteristics of the inventive 'HEGHE02' variety are stable from generation to generation; clones of the variety produced by asexual reproduction maintain the distinguishing characteristics of the original plant.

SUMMARY OF THE INVENTION

'HEGHE02' is a distinctive variety of *Hemigraphis alternata* which is characterized by yellow and green leaf variegation, large leaf size, and a dense growth habit.

BOTANICAL DESCRIPTION OF THE PLANT

Figure 1:
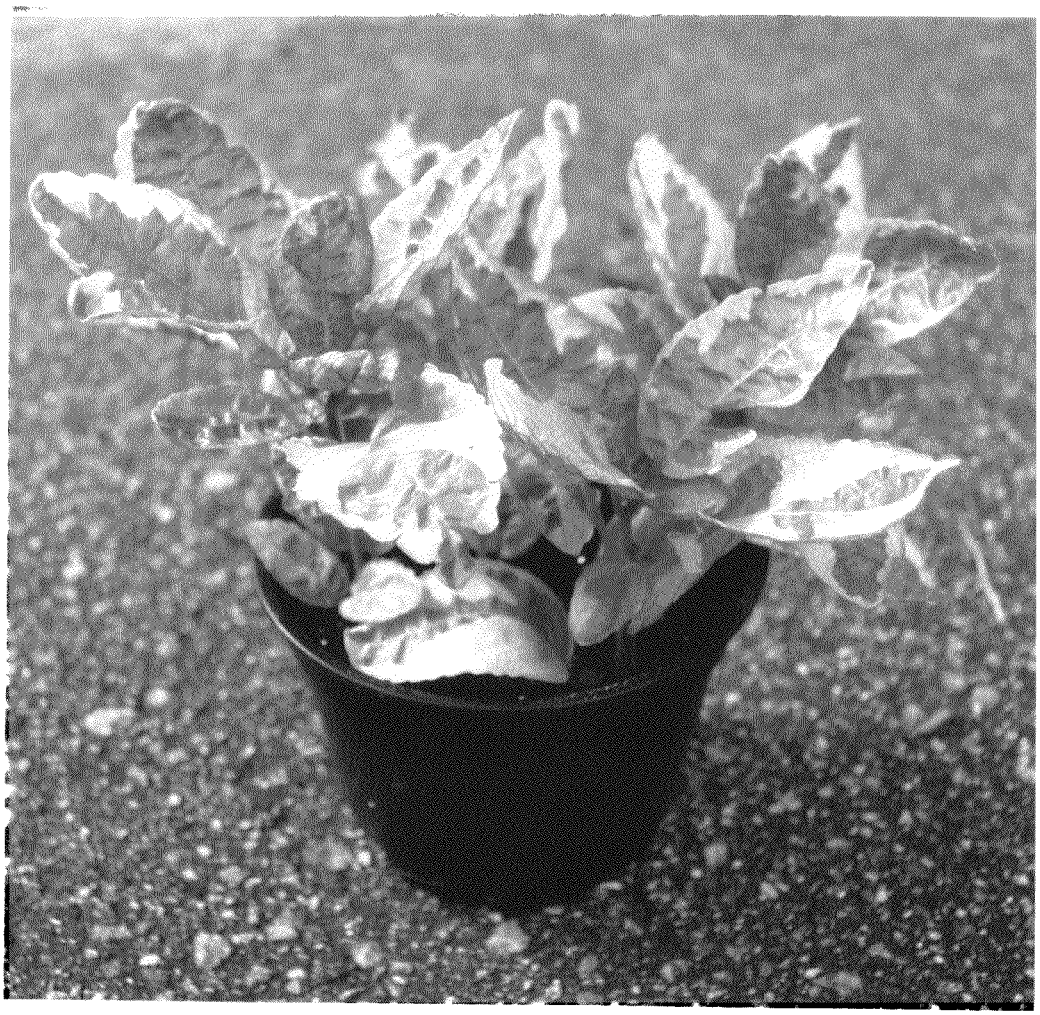
FIG. 1 illustrates an exemplary 5 week-old 'HEGHE02' plant.
Figure 2:
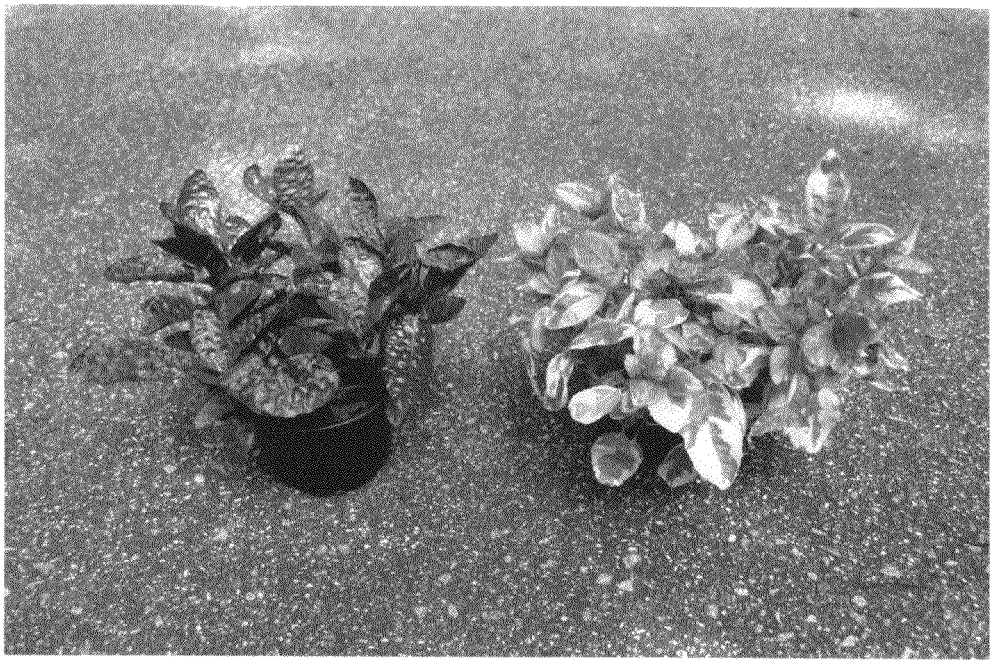
FIG. 2 illustrates a comparison of 'HEGHE02' (on right) with the parent, *Hemigraphis alternata* 'Exotica', on left. Both plants are 28 weeks old.
Figure 3:
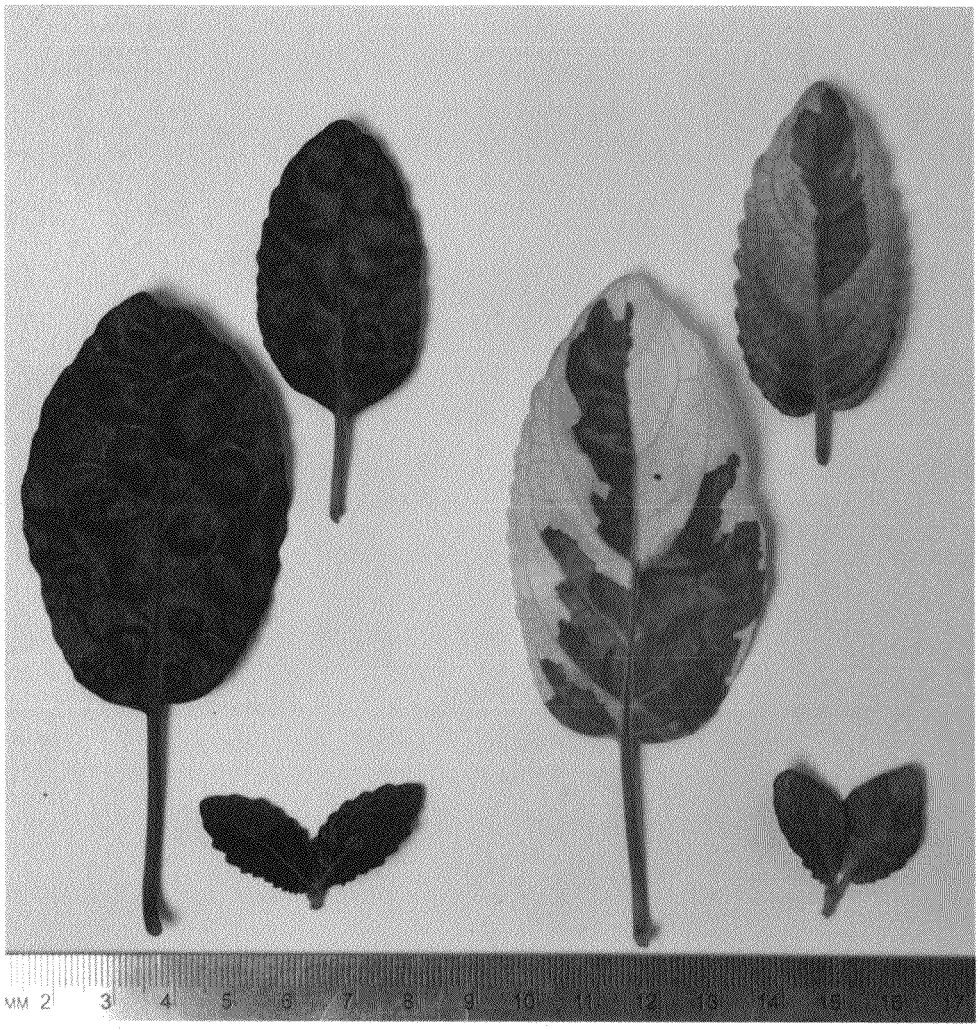
FIG. 3 illustrates the exemplary foliage variegation of 'HEGHE02' (on right) at various stages of development, from juvenile to intermediate to mature, by comparison with the parent, on left. Perspective is adaxial.

The following is a detailed botanical description of a new and distinct variety of a *Hemigraphis alternata* ornamental plant known as 'HEGHE02'. Plant observations were made on plants grown at a commercial greenhouse in Apopka, Fla. Unless indicated otherwise, the descriptions disclosed herein are based upon observations made from 28 week-old, greenhouse-grown 'HEGHE02' plants grown from rooted cuttings in 15 cm nursery pots filled with soilless potting media, maintained with periodic applications of liquid slow-release fertilizer with a 20-20-20 (Nitrogen-Phosphorous-Potassium) formulation at a rate of 225 parts-per-million of Nitrogen. Plants were regularly watered with drip irrigation (pH 6.0) and systemic fungicides and insecticides were applied as pest treatment thresholds dictated. Approximate average temperature range in the greenhouse was between 70 and 80 degrees Fahrenheit and light levels ranged from 1500 to 1800 Foot-candles. No plant growth regulators were used.

Those skilled in the art will appreciate that certain characteristics will vary with older or, conversely, younger plants. 'HEGHE02' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on *The Royal Horticultural Society Colour Chart,* The Royal Horticultural Society, London, 1986 edition. Note that generic color descriptions such as 'purple' do not exist in the R.H.S. charts and the corresponding R.H.S. colors are quoted.

'HEGHE02' is a perennial *Hemigraphis alternata* plant which is a spontaneous mutation of *Hemigraphis alternata* 'Exotica', selected for its yellow and green leaf variegation, large leaf size, and a dense growth habit. These features and other characteristics are apparent from the description provided below.

Growth Habit, Dimensions and Color

Plant description:

- *Plant habit.*—Creeping to mounding herbaceous perennial with a fast growth rate.
- *Height.*—16 cm as measured.
- *Width.*—35 cm as measured.
- *Natural bloom period.*—Sporadic; may bloom at any time of year in warm environments.
- *Hardiness.*—USDA Zone 10 to 11.
- *Environmental tolerances.*—In common with the species; does not tolerate drought, high salinity, low temperatures or frost.
- *Pest and disease susceptibility or resistance.*—In common with the species; none of note.
- *Propagation.*—Propagation is accomplished using vegetative cuttings and plants root well without the use of a rooting compound or hormone. Time to initiate root development is approximately 7 to 12 days at approximately 70 degrees Fahrenheit, with light levels of 1800-2000 Foot-candles.

Roots: Fibrous and freely branched and also exhibits adventitious rooting from aerial nodes.

Stem:

- *Branching and habit.*—Branches are sprawling and prostrate at ground-level and eventually becoming ascending, exhibiting a stolon-like habit. Freely branching with numerous branches ascending from all nodes along stolon-like stems.
- *Stem strength.*—Weak; little rigidity.
- *Shape.*—Cylindrical.
- *Stem color.*—A combination of red-purple 63C and yellow-green 146D, with the predominant color being yellow-green 146D.
- *Stem dimensions.*—Longest stem measured at 140 mm. Stem diameter ranges from 3 to 5 mm at the base.
- *Stem surface.*—Soft and pubescent.
- *Internode length.*—Highly variable throughout the plant; generally ranges from 10 to 20 mm between the first and second aerial nodes.

Foliage:

- *Type.*—Perennial.
- *Division.*—Simple.
- *Arrangement.*—Opposite, decussate.
- *Orientation.*—Upward and outward in juvenile and intermediate foliage and becoming close to horizontal in mature foliage.
- *Attachment.*—Petiolate.
- *Shape.*—Ovate.
- *Apex.*—Broadly acute.
- *Base.*—Broadly Cuneate to acute.
- *Cross-section.*—Involute.
- *Venation.*—Reticulate.
- *Vein color (adaxial surfaces).*—Basal portion of the midrib is red-purple 63B, becoming green 138D along the apical half of the midrib. All secondary veins are green 138D, except becoming green-white 157B at and near the leaf margins.
- *Vein color (abaxial surfaces).*—Green 145B near the petiole, becoming red-purple 70A throughout most of the leaf surface.
- *Margins.*—Crenate and slightly involute.
- *Texture.*—Puckered or blistered leaf surface, i.e. bullate; both adaxial and abaxial surfaces are pubescent.
- *Mature leaf dimensions.*—Approximate length 90 mm, average width 55 mm.
- *Leaf color (adaxial surface).*—Juvenile: variegated with an irregular pattern of yellow-green 152A at and near the midrib, becoming yellow-green 152D to 151A at and near the leaf margin; Intermediate foliage: variegated with an irregular pattern of yellow-green 146B to 146C at and near the midrib, becoming yellow 11C at and near the leaf margin; Mature: variegated with an irregular pattern of yellow-green 146C at and near the midrib, becoming orange-white 159C at and near the leaf margin.
- *Leaf color (abaxial surface).*—Juvenile: greyed-purple 186B; Intermediate foliage: variegated with an irregular pattern of yellow-green 147D at and near the midrib, becoming orange-white 159C at and near the leaf margin; Mature: variegated with an irregular pattern and exhibiting a combination of red-purple 70A and 71A at and near the midrib, with a combination of yellow 11D, red-purple 63C and 63D at and near the leaf margin.
- *Petiole.*—Longest measured petioles are 55 mm; width is 3 mm. Color is a combination of red-purple 63C and yellow-green 146D, with the predominant color being red-purple 63C; lightly pubescent.
- *Stipules.*—None.

Inflorescence:

- *Inflorescence type.*—Spike inflorescence with few sessile flowers; typically only one flower is fully opened at any given time. Aspect of flowers is upward to slightly pendulous.
- *Inflorescence dimensions.*—Approximately 4 cm long and 5.5 cm wide.

Bud:

- *Flower bud shape.*—Spherical with an obovate profile.
- *Flower bud length.*—Approximately 5.0 mm.
- *Flower bud diameter.*—Approximately 2.25 mm, at the widest point.
- *Bud color.*—White RHS 155D.

Flowers:

*Flowering quantity*.—Approximately 2 to 4 flowers per inflorescence.

*Natural flowering season*.—Naturally blooming continuously from early spring through late summer.

*Pedicel*.—None; flowers are sessile.

*Calyx*.—Quantity of sepals — 5 sepals, fused at the base. Sepal dimensions — Approximately 7 mm long and 1.5 mm wide. Sepal color — Greyed-purple RHS 187A. Sepal apex — Narrowly acuminate. Sepal margin — Entire.

*Corolla*.—Simple flower consisting of 5 petals, fused at the base, forming a corolla tube; the approximate diameter is 7.5 mm and the approximate depth is 8.0 mm, including the corolla tube. Flowers are not persistent and are non-fragrant. Petal description — Arrangement — Rotate. Quantity — Five. Length — Unfused portion of the petal measures approximately 4.0 mm long. Width — Unfused portion of the petal measures approximately 3.0 mm wide. Apex — Broad acute. Margin — Entire. Texture — Glabrous, smooth and with a matte appearance. Color (adaxial surface) — White RHS 155D. Color (abaxial surface) — White RHS 155D.

Reproductive organs:

*Stamens*.—Number — Four. Filament dimension — Approximately 6 mm long and 0.25 mm wide. Filament color— White; near RHS 155A and tinged with red-purple RHS 70A. Anther shape — Comprised of two pollen chamber of equal size; general shape is oblong. Anther length — Approximately 0.75 mm. Anther color — Near red-purple RHS 70A along the dorsiventral divide; remainder of anther near white RHS 155A. Pollen — None observed.

*Pistil*.—Pistil number — One. Pistil dimensions — Approximately 7 mm, including the style, and 0.25 mm wide. Stigma shape — Club-shaped. Stigma color — White; near RHS 155A and tinged with red-purple RHS 70A. Ovary Position — Superior.

Fruit and seed production: None observed.

Comparison of HEGHE02 with Other Varieties of *Hemigraphis alternata*

By comparison with the parent, the leaves of 'HEGHE02' are characterized by a green and yellow variegated adaxial leaf surface as described above, whereas the adaxial leaf surface of the parent is a solid color, corresponding to yellow-green 147A in juvenile and intermediate foliage and becoming greyed-purple (approximately 187A) at maturity. Likewise, the abaxial leaf surface in 'HEGHE02' is also variegated as described herein, whereas the abaxial leaf surface of the parent is a solid color, corresponding to a combination of greyed-purple 186A and purple 79B in juvenile and intermediate foliage and becoming greyed-purple 187A and 79A in mature foliage. The stem color of 'HEGHE02' is a combination of red-purple 63C and yellow-green 146D, with the predominant color being yellow-green 146D whereas the stem color of the parent is a combination of yellow-green 146D and greyed-purple 187A, with the predominant color being greyed-purple 187D. As described herein, 'HEGHE02' exhibits an almost stolon-like habit with a multitude of stems running horizontally at the soil surface whereas the stems of the parent plant are ascending as they emerge from the soil. While both the parent and 'HEGHE02' are approximately the same height, the stem internode length in 'HEGHE02' is shorter than that of the parent. Stem internode length between the first and second aerial internodes of 'HEGHE02' ranges from 10-20 mm whereas in the parent the length of the same ranges from 30 to 50 mm. Also, the mature leaves of 'HEGHE02' are larger than those of the parent. The dimensions of mature leaves of 'HEGHE02' are, on average, 90 mm long by 55 mm wide, whereas the largest measured leaves of the parent are 80 mm long and 45 mm wide. The combination of a stolon-like branching habit, shortened stem internodes and larger leaves gives 'HEGHE02' a more dense appearance when compared to the parent.

'HEGHE02' is similar to the commercial variety *Hemigraphis alternata* 'HEGHE01' (U.S. Plant patent application Ser. No. 13/987,386) in many horticultural characteristics. 'HEGHE02', however, has a more decumbent growth habit, larger leaves, a lightly bullate leaf texture, slightly involuted leaf margins, and leaves with green and yellow variegation. 'HEGHE02' exhibits dimension of approximately 16 cm tall and 35 cm wide and stems with a decumbent, stolon-like growth habit, whereas 'HEGHE01' exhibits dimensions of approximately 22 cm tall and 28 cm wide and stems with an upright attitude. Mature leaves of 'HEGHE02' exhibit dimensions of approximately 90 mm long and 55 mm wide, whereas mature leaves of 'HEGHE01' exhibit dimensions of approximately 80 mm long and 45 mm wide. The leaf texture of 'HEGHE01' is highly bullate, whereas the expression of this characteristic is less pronounced in 'HEGHE02'. Juvenile and intermediate leaves of 'HEGHE01' exhibit a highly involute cross-section by comparison with 'HEGHE02' which exhibits only a slightly involute leaf cross-section. The adaxial leaf surface of 'HEGHE02' is characterized by green and yellow variegation and a pale pink coloration of the abaxial surface, whereas the leaves of 'HEGHE01' are characterized by pink and green to white and green variegation of the adaxial leaf surface, and a generally bright pink appearance to the abaxial leaf surface.

That which is claimed is:

1. A new and distinct variety of *Hemigraphis alternata* plant named 'HEGHE02', substantially as described and illustrated herein.

* * * * *